United States Patent [19]

Nagai

[11] Patent Number: 5,592,959

[45] Date of Patent: Jan. 14, 1997

[54] PIPET WASHING APPARATUS

[75] Inventor: Takaaki Nagai, Kobe, Japan

[73] Assignee: TOA Medical Electronics Co., Ltd., Hyogo-ken, Japan

[21] Appl. No.: 359,994

[22] Filed: Dec. 20, 1994

[30] Foreign Application Priority Data

Dec. 20, 1993 [JP] Japan .................................. 5-320152
Nov. 24, 1994 [JP] Japan .................................. 6-289790

[51] Int. Cl.⁶ .................................................. B08B 9/00
[52] U.S. Cl. ................................ 134/169 R; 73/864.22; 134/170
[58] Field of Search ......................... 134/169 R, 170; 141/90, 91; 73/864.22; 15/302

[56] References Cited

U.S. PATENT DOCUMENTS

| | | |
|---|---|---|
| 3,552,212 | 1/1971 | Ohlin . |
| 3,719,086 | 3/1973 | Bannister et al. . |
| 3,748,911 | 7/1973 | Rousselet et al. . |
| 3,911,749 | 10/1975 | Hendry ............................ 73/864.22 |
| 4,495,149 | 1/1985 | Iwata et al. . |
| 4,574,850 | 3/1986 | Davis .............................. 141/90 X |
| 5,408,891 | 4/1995 | Barber et al. ..................... 73/864.22 |

FOREIGN PATENT DOCUMENTS

| | | |
|---|---|---|
| 602802 | 6/1994 | European Pat. Off. . |
| 61-82275 | 5/1986 | Japan . |
| 63-139256 | 6/1988 | Japan . |
| 2075672 | 11/1981 | United Kingdom ............... 73/864.22 |

Primary Examiner—Philip R. Coe

[57] ABSTRACT

A washing apparatus includes a pipet-outer-wall washing member embedding a through-hole in which a pipet is loosely inserted, a supply path for supplying washing solution to the through-hole, and a discharge path for discharging waste liquid from the through-hole. It further includes a pipet-interior washing device which connects to the pipet. A washing solution storage chamber is connected to the supply path in the pipet-outer-wall washing member and to the pipet-interior washing device and a suction device is connected to the discharge path of the washing member. The sucking device is used for sucking-up waste liquid which exits the through-hole at a side wall thereof. A waste liquid storage chamber is connected to the discharge path. Finally, a drive device causes at least one of the washing member and the pipet to move relative to the other to vary the relative position of the washing member versus the pipet to thereby allow for washing of the entire pipet. Further, the through-hole includes a narrow diameter portion having a narrow clearance for the pipet and a wide diameter portion, formed below the narrow diameter portion, with a clearance for the pipet that is wider than that of the narrow diameter portion. Additionally, the supply path is linked to a side wall of the wide diameter portion, whereas the discharge path is linked to a side wall of the narrow diameter portion.

19 Claims, 4 Drawing Sheets

PIPET WASHING APPARATUS

BACKGROUND OF THE INVENTION

1. Field of the Invention

The present invention relates to a pipet washing apparatus, more particularly, to a pipet washing apparatus for washing a liquid-sampling pipet used for sucking a liquid sample such as blood.

2. Description of the Prior Art

In the field of washing apparatuses for washing a pipet used for sucking a liquid sample such as blood, a washing apparatus having a through-hole for loosely coupling a pipet therein is well known. Such a washing apparatus washes out sample liquid and dust adhered to the pipet by feeding washing solution to the through-hole by way of shifting itself along the pipet.

The pipet washing apparatus cited above was already known as of the early 1970's. Various improvements have since been proposed. For example, improved pipet washing apparatuses were proposed in Japanese Laid-Open Patent Publication No. SHO 63(1988)-139256 and Japanese Laid-Open Utility Model Publication No. SHO 61 (1986)-82275. Either of these prior art apparatuses washes both the inner and outer walls of a pipet.

More particularly, according to the first Patent Publication cited above, an upper portion of a through-hole of a washing apparatus (termed a "washing case") guides a pipet (termed a "needle") in conjunction with a sealing device. A large-diameter cylindrical washing chamber is disposed in a lower portion of the washing apparatus. Washing solution is fed to an upper portion of the washing chamber before being sucked via a lower portion thereof. An end piece having a narrow opening is set in the bottom end of the washing chamber. When washing is underway while shifting the pipet, the outer wall of the pipet is washed by feeding and discharging washing solution to and from the washing chamber. The inner wall of the pipet is also washed by way of a reversing flow of washing solution from the pipet when the tip (bottom end) of the pipet is positioned near an outlet of the washing chamber.

According to the latter Utility Model Publication cited above, a washing apparatus (termed a "washing chip") has a through-hole whose upper portion is narrow as compared with a wide lower portion. Washing solution is fed to an upper portion of the wide lower portion before being discharged from the lower portion. When washing an inner wall of a sample pipet (termed a "sucking tube"), the tip (bottom end) of the sample pipet is positioned in a waste-fluid sucking passage in the lower portion of the washing apparatus.

Generally, sample liquid adhered to an outer wall of a pipet flows downward because of its own weight before being collected at the tip portion of the pipet. In particular, such a sample liquid of high viscosity (e.g. blood) adheres to an outer wall of the pipet in large amounts. According to the washing operation proposed by the first Patent Publication cited above, because of a narrow opening at the lower portion of the through-hole, sample liquid also adheres to the lower opening edge of an outer portion of the opening. Washing becomes a critical problem because sample liquid adhered to the lower opening edge of the through-hole cannot come into contact with the washing solution.

This problem can be solved by expanding the lower opening of the through-hole. However, this in turn raises a further problem because of incomplete collection of the washing solution. The washing solution collecting portion is open to the atmosphere via the lower opening of the through-hole, since sucking a gas involves less resistance than sucking a liquid, collection of air via the lower opening of said through-hole occurs preferentially to collection of liquid. This results in incomplete collection of washing solution when the lower opening of the through-hole is expanded.

There is a common problem in the above-cited prior art patents in that both of said prior art washing systems need a large amount of washing solution to properly wash a pipet.

This invention has been achieved to fully solve the above problems.

SUMMARY OF THE INVENTION

The object of the invention is to provide an improved pipet washing apparatus capable of fully and effectively executing removal of a sample adhered to a pipet and the collection of pipet washing solution using a limited amount of washing solution.

The object of the invention is fulfilled by a pipet washing apparatus comprising: a pipet; a pipet-outer-wall washing member embedding a through-hole in which said pipet is loosely inserted, a supply path for supplying washing solution to said through-hole, and a discharge path for discharging waste liquid from said through-hole; a pipet-interior washing means which is connected to said pipet; a washing solution storage chamber connected to said supply path in said pipet-outer-wall washing member and said pipet-interior washing means; a suction means which is connected to said discharge path of said washing member and used for sucking up waste liquid from said pipet; a waste liquid storage chamber which is connected to said discharge path; and a drive means which causes either or both of said washing member and said pipet to shift position in order to vary the relative position of said washing member and said pipet; said through-hole providing a narrow diameter portion having a narrow clearance against said pipet and a wide portion formed below said narrow diameter portion and having clearance for said pipet that is wider than that of said narrow diameter portion; said supply path being linked with said wide portion and said discharge path being linked with said narrow diameter portion.

The pipet washing apparatus according to the invention is characterized by the above structure, and accordingly, the removal and collection of sample adhered to a pipet and the collection of pipet washing solution can be fully and effectively achieved.

These and other objects of the present application will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

A pipet to be cleaned by the present invention is used to suck liquid samples such as blood stored in sample containers for analysis. For example, such a pipet may be made of stainless steel and structured by way of forming a hollow needle having a length of 50–150 mm, an outer diameter of 1.0–3.0 mm, and an inner diameter of 0.5–2.5 mm.

A cylindrical member (made from PVC resin, for example) is used for the pipet-outer-wall washing member, which washes an outer wall surface of the pipet and is supplied with a washing solution. The washing member is provided with a through-hole, a supply path, and a discharge path, and the through-hole is disposed substantially perpendicular to the longitudinal axis of the pipet. The pipet is loosely inserted in the through-hole.

The through-hole, the supply path and the discharge path may be of any optional sectional form such as circular, elliptical or square, but a circular form is preferable for washing efficiency. When providing a circular sectional form for the through-hole, the through-hole diameter is determined in accordance with an outer diameter of the pipet, the kind of washing solution, and other factors. The through-hole consists of a narrow diameter portion having a relatively narrow clearance for the pipet and a portion, below the narrow diameter portion, having a relatively wide clearance for the pipet.

To guide the pipet into the narrow diameter portion a tapered portion may be provided between the narrow diameter portion and the wide portion so as to interlink both portions. Also the opening of the wide portion (i.e., the opening on the bottom side of the through-hole) may be chamfered.

The supply path supplies washing solution to the through-hole at the wide portion of the through-hole. The discharge path discharges waste liquid including used washing solution and liquid sample from the through-hole collected at an aperture at the narrow diameter portion of the through-hole. Although it is desired that both the supply path and the discharge path be disposed orthogonal to the through-hole (i.e. substantially level) and parallel with each other, such an arrangement is not required.

The pipet-interior washing device is connected to one end portion, for example the upper end portion, of the pipet so that washing solution can be supplied to the interior of the pipet. An example of the pipet-interior washing device includes a tube for supplying washing solution and a pump connected to this tube via a valve. As in an embodiment to be described later, a sampling quantification unit may be provided between the upper end portion of the pipet and the washing solution supply tube. In this case, the functions of quantification of sample versus washing of the interior of the pipet may be switched by operating the above-referred valve and pump.

The washing solution to be fed to the supply path of the washing member and to the pipet-interior washing device is stored in a washing solution storage device. The washing solution storage device may include one or more chambers, such as washing solution storage chamber 24 to be described later.

The suction device is connected to the discharge path of the washing member and can act to discharge waste liquid generated by washing the outer wall and the interior of the pipet. An example of the suction device is a suction pump for generating negative pressure.

The waste liquid is stored in a waste liquid storage device. The waste liquid storage device may include one or more chambers, such as waste liquid storage chamber 29 to be described later.

The drive device causes either or both of the washing member and the pipet to shift positions when a liquid sampling inlet at one end of the pipet is inserted in the through-hole. Next, the drive device shifts the relative position of the washing member and the pipet. The drive device may only shift the washing member in the vertical direction as the pipet itself remains still, or it may cause both the pipet and the washing member to shift positions in opposition to each other.

It is desired that the drive device causes the sampling inlet of the pipet to be positioned at the narrow diameter portion of the through-hole of the washing member. By properly controlling this operation of the pipet-interior washing device and by activating the suction device simultaneously with the positioning of the sampling inlet of the pipet at the narrow diameter portion of the through-hole, the interior of the pipet can be properly washed and the waste liquid can be thoroughly sucked up.

For example, the drive device may comprise the following: a drive motor having a horizontal shaft and capable of rotating in the normal and reverse directions; a first pulley connected to the rotating shaft; a second pulley disposed above or below the first pulley; a drive belt engaged between the first and second pulleys; and supporting members which interconnect and hold the drive belt and the washing member in order to vertically shift only the washing member.

In the event that the drive device is so structured that it shifts only the washing member in the vertical direction, then the washing member is initially positioned at an upper end portion of the pipet and the sampling inlet of the pipet, i.e., the bottom end portion, is immersed in a liquid sample so that the liquid sample can be sucked up. After this suction process is completed, the washing member is gradually lowered by the drive device.

As the washing member descends, washing solution is supplied to the supply path of the washing member from the washing solution storage device. Then, washing solution is supplied to the wide portion of the through-hole via the supply path. Next, washing of the outer wall surface of the pipet is executed.

Simultaneously with the outer wall surface washing, suction is transmitted to the discharge path of the washing member by the suction pump to affect thereby the narrow diameter portion of the through-hole. As a result, liquid (including washing solution and sample) is attracted by suction pressure and then is discharged from the discharge path via the narrow diameter portion. The waste liquid discharged from the discharge path is stored in the waste liquid storage device.

The through-hole of the washing member accommodating the inserted pipet is so arranged that the upper portion thereof corresponds to the narrow diameter portion and the lower portion thereof corresponds to the wide diameter portion. Accordingly, even when a large amount of liquid sample adheres to the pipet, the liquid sample freely enters the wide portion of the through-hole and is washed by washing solution supplied to this portion. Thus, even the slightest amount of liquid sample cannot adhere to an opening edge on the bottom side of the through-hole.

More particularly, the discharge path of the washing member is linked with the narrow diameter portion of the through-hole. Furthermore, the clearance between the narrow diameter portion and the pipet is quite narrow. Since the narrow portion is affected by suction (negative) pressure, a negative pressure affected zone is evenly generated around the periphery of the pipet. This in turn causes liquid in the wide portion of the through-hole to smoothly flow into the clearance between the narrow diameter portion and the pipet from the periphery of the pipet. Consequently, since liquid in the narrow clearance portion is entirely affected by substantially even suction pressure, such liquid is collected in the discharge path and the waste liquid is externally discharged.

Next, a method of washing the inner wall surface of the pipet will be described. Eventually, the sampling inlet (bottom end) of the pipet is positioned slightly above the bottom of the narrow diameter portion of the through-hole. While this condition remains, washing solution is fed at the upper end portion of the pipet to the interior of the pipet. Since the clearance between the narrow diameter portion and the pipet is relatively narrow, the washing solution and liquid sample discharged from the pipet flow downward via the inner wall surface of the narrow diameter portion of the through-hole. Note that, if there were substantial clearance as in the case of a conventional pipet washing apparatus, this would permit the discharged washing solution and liquid sample to form drops that fall downward without transiting along the inner wall surface of the narrow diameter portion and which thereby would not be fully collected via suction pressure as discussed above.

Simultaneous with the discharge of washing solution from the sampling inlet of the pipet, washing solution is also fed from the supply path which opens to the wide portion of the through-hole of the washing member. Since the majority of the upper portion of the narrow diameter portion is blocked by the pipet, washing solution fed from the supply path located below the washing member is affected by the suction of the discharge path. Thus washing solution supplied to the wide portion and liquid sample from the pipet are both smoothly led to the discharge path by the negative pressure of the suction pump before eventually being collected.

The diameter of the narrow diameter portion and the diameter of the wide portion of the through-hole can be optimized depending on the volume of washing solution desired and the capacity to collect it. For example, it is suggested that the diameter of the narrow diameter portion range from 110% to 120% of the outer diameter of the pipet, whereas a diameter of the wide portion may range from 150% to 250% of the outer diameter of the pipet.

As a result of executing the above processes, both the inner and outer wall surfaces of the pipet and the surface of the through-hole are thoroughly washed. Also, as a result of suction from the discharge path, liquid drops are removed from outer wall surface of the pipet and the through-hole of the washing member.

Next, the washing member ascends until it is returned to its original position. Suction is applied to the discharge path even while the washing member ascends. This ensures further removal of any remaining washing solution and liquid sample adhered to the outer wall surface of the pipet.

PREFERRED EMBODIMENTS OF THE INVENTION

Referring now to the accompanying drawings, three embodiments of the invention will be described below. It should be understood, however, that the scope of the invention is by no means limited to the following three embodiments; rather the scope is as defined in the claims.

Embodiment 1

Figure 1:
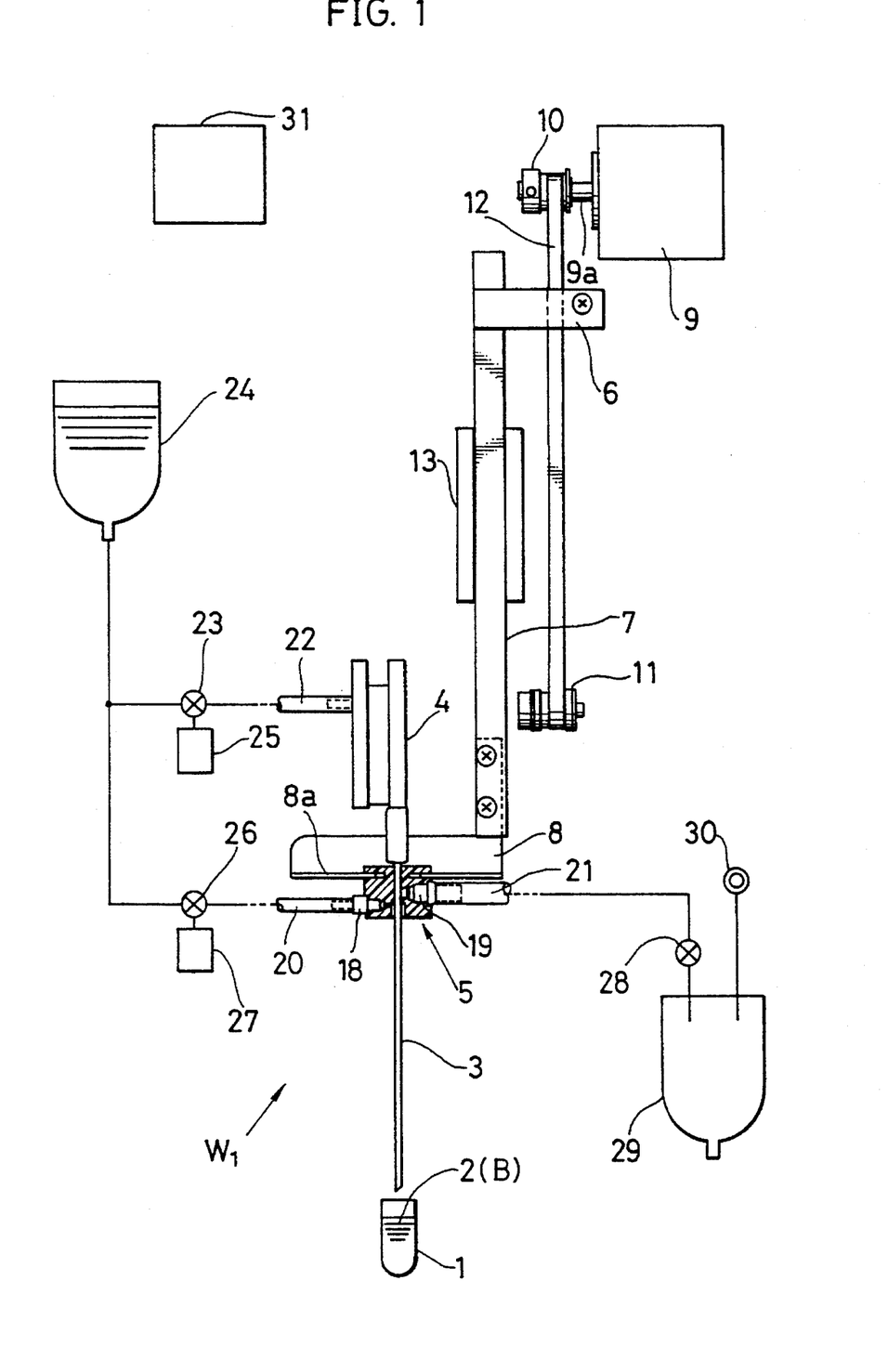
FIG. 1 is an overall schematic block diagram of the pipet washing apparatus according to a first embodiment of the invention.
Figure 2:
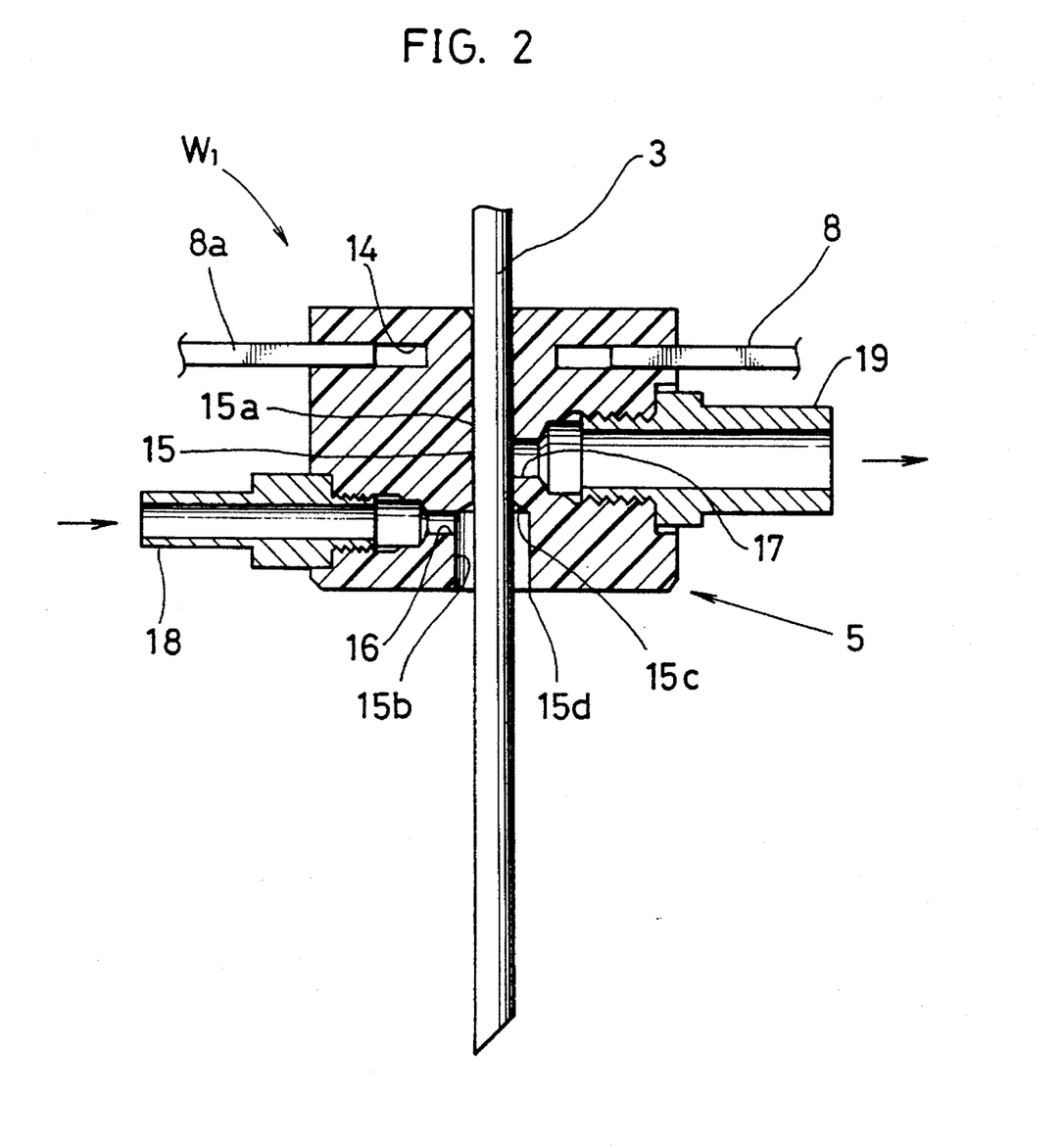
FIG. 2 illustrates a sectional view of structural members of the inventive pipet washing apparatus in the course of washing an outer wall surface of a pipet.
Figure 3:
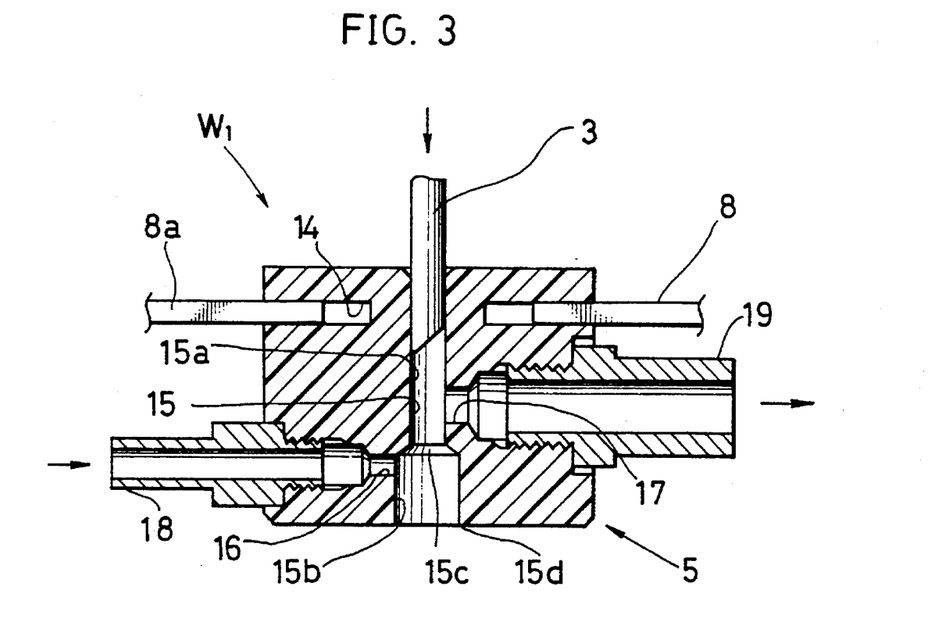
FIG. 3 is a sectional view of structural members of the inventive pipet washing apparatus in the course of washing an inner wall surface of the pipet.

Referring now to FIGS. 1 through 3, structural features of a pipet washing apparatus W1 according to a first embodiment of the invention will be described below. The reference numeral 1 shown in the drawings designates a test-tube type sample container. The sample container 1 stores blood sample 2(B) subject to analysis. The reference numeral 3 designates a pipet made of stainless steel for sampling blood 2. The pipet 3 is of circular sectional form having a 2.0 mm outer diameter and is vertically disposed. An upper end portion of the pipet 3 is linked with a sampling quantification unit 4 that serves as a device for estimating sample. The pipet 3 is loosely inserted in a cylindrical through-hole of washing member 5 made from PVC resin.

The washing member 5 is held by vertically movable first, second, and third supporting members 6, 7, and 8, which respectively function as part of a drive device. The reference numeral 9 designates a drive motor serving as part of the drive device. The motor 9 is rotatable in the normal and reverse directions and is provided with a rotary shaft 9a which is horizontally disposed. The rotary shaft 9a is connected to an upper pulley 10 forming part of the drive device. A lower pulley 11 sharing part of the drive device is disposed below the upper pulley 10. A drive belt 12 forming part of the drive device is engaged between the upper and lower pulleys 10 and 11.

The first supporting member 6 consists of a pair of rectangular plates which are substantially horizontally disposed and secured to the drive belt 12 with screw members that nip the drive belt 12. The second supporting member 7 consists of a vertically disposed rod member. The first supporting member 6 is secured to an upper end portion of the second supporting member 7. The third supporting member 8 is secured to a bottom end portion of the second supporting member 7 with screw members. The second supporting member 7 is slidably inserted in a guide rail sharing part of the drive device. The third supporting member 8 is disposed above the washing member 5 and is integrated therewith.

A ring-shaped groove 14 (FIG. 2) is formed in an upper lateral wall of the washing member 5. A horizontal plate portion 8a of the third supporting member 8 is inserted in the groove 14 in the horizontal direction with spacewise allowance. There is no spacewise allowance in the vertical direction. In other words, the washing member 5 can shift itself solely in the horizontal direction against the third supporting member 8. Accordingly, even when the position of the pipet 3 deviates after loosely being inserted in the washing member 5, positional deviation of the pipet 3 can be corrected by horizontally shifting the washing member 5 to an optimal position.

The washing member 5 embeds a vertically formed through-hole 15 in which the pipet 3 is loosely insertable, a horizontally formed supply path 16 for feeding washing solution to the through-hole 15, and a horizontally formed discharge path 17 for discharging washing solution and blood sample B from the through-hole 15. The through-hole 15, the supply path 16, and the discharge path 17, are respectively of circular sectional form.

The through-hole 15 has a narrow diameter portion 15a with a narrow clearance for the pipet 3 and a wide diameter portion 15b formed below the narrow diameter portion 15a and with a wide clearance for the pipet 3. Tapered portion 15c is formed between the narrow diameter portion 15a and the wide diameter portion 15b. The length (height) of the narrow diameter portion 15a corresponds to about 70% of the height of the washing member 5. More specifically, the diameter of the narrow diameter portion 15a corresponds to 115% (2.3 mm) of the outer diameter of the pipet 3. The length (height) of the wide diameter portion 15b corresponds to about 25% of the height of the washing member 5. More specifically, the diameter of the wide diameter portion 15b corresponds to 200% (4.0 mm) of the outer diameter of the pipet 3. The height of the tapered portion 15c corresponds to about 5% of the height of the washing member 5.

The diameter of the supply path 16 corresponds to about 55% (1.1 mm to 1.2 mm) of the outer diameter of the pipet 3. The inner end of the supply path 16 opens to an upper end portion of the wide diameter portion 15b. The diameter of the discharge path 17 corresponds to about 105% (2.1 mm to 2.2 mm) of the outer diameter of the pipet 3. The inner end of the discharge path 17 is open and is near the bottom end of the narrow diameter portion 15a.

A small nipple 18 and a large nipple 19 are horizontally secured to the washing member 5 by partial embedment. An inner end of the small nipple 18 is connected to an outer end of the supply path 16. An end of a second tube 20 for supplying washing solution is connected to an outer end of the small nipple 18. An inner end of the large nipple 9 is connected to an outer end of the discharge path 17. An end of a tube 21 for discharging washing solution and sample is connected to an outer end of the large nipple 19.

An end of a first tube 22 for feeding washing solution is connected to the sampling unit 4. The other end of the first tube 22 is connected to a first valve 23. The first valve 23 is connected to a washing solution storage chamber 24 and a suction/discharge type first pump 25. Using the first valve 23 and the first pump 25, washing solution stored in the washing solution storage chamber 24 is supplied to the interior of the pipet 3 via the first tube 22 and the sampling quantification unit 4.

The other end of the second tube 20 is connected to a second valve 26. The second valve 26 is connected to the washing solution storage chamber 24 and a suction/discharge type second pump 27. Washing solution stored in the washing solution storage chamber 24 is supplied to the supply path 16 of the washing member 5 via the second tube 20 and the small nipple 18 by means of the second valve 26 and the second pump 27.

The other end of the tube 21 is connected to a third valve 28. The third valve 28 is connected to a waste liquid storage chamber 29 for storing waste liquid generated by washing solution and sample discharged from the through-hole 15 of the washing member 5. The waste liquid storage chamber 29 is connected to suction pump 30 serving as negative pressure generating source for discharging washing solution and sample. When operation of the suction pump 30 is activated, negative (suction) pressure is generated in the discharge path 17 via the waste liquid storage chamber 29, the third valve 28, the discharge tube 21, and the large nipple 19.

Reference numeral 31 shown in FIG. 1 designates a controller. The controller 31 properly controls normal/reverse rotation and stopping of the drive motor 9, opening and closing of the first, second, and the third valves 23, 26, and 28, operation of the first and second pumps 25 and 27, and operation of the suction pump 30.

Next, the functioning of respective component members in the course of washing the pipet 3 with the pipet washing apparatus W1 is described below.

Sampling of analyzable blood 2 is executed via the following processes. As shown in FIG. 1, while the washing member 5 is positioned at the tip of the pipet 3, the pipet 3 is immersed in blood 2 stored in the test container 1. Next, the first valve 23 is opened in order that the sampling valve 4 can be connected to the first pump 25. Next, the first pump 25 is switched over to suction mode and then activated. Accordingly, blood 2 is sucked into the sampling quantification unit 4 via the pipet 3. Approximately 100 μ liter (=0.1 milliliter) of blood 2 is sampled.

After executing blood sampling, the inner and outer wall surfaces of the pipet 3 are adhered with blood B. Washing of the outer wall surface of the pipet 3 is executed by way of the following: Initially, the second valve 26 is opened in order that the washing solution storage chamber 24 can be connected to the second pump 27. When the second pump 27 is switched over to a suction mode and then activated, washing solution stored in the storage chamber 24 is sucked into the second pump 27. Next, the second valve 26 is opened so that the second pump 27 can be connected to the second tube 20. Next, the second pump 27 is switched over to a discharge mode and then activated. As a result, washing solution in the second pump 27 is supplied to the supply path 16 of the washing member 5 via the second tube 20 and the small nipple 18. Supply of washing solution is executed for about 3 through 5 seconds at approximately 0.3 ml/sec. of flow rate.

Next, the drive motor 9 rotates in the normal direction to cause the belt 12 to be driven in the normal direction. This in turn causes the first, second, and the third supporting members 6, 7, and 8 to gradually descend. Thus, the washing member 5 gradually descends from the uppermost position of the pipet 3 to effect washing of the outer wall surface of the pipet 3. The washing member 5 descends at 15–30 mm/sec. of speed.

After being delivered to the supply path 16 of the washing member 5, during the descending movement of the washing member 5, washing solution is injected inside the wide diametral portion 15b of the through-hole 15. Simultaneously, a suction pump 30 is activated to generate −250 mmHg of negative pressure in the discharge path 17. The negative pressure (being lower than atmospheric pressure by 250 mmHg) affects the narrow diameter portion 15a of the through-hole 15 accommodating the inserted pipet 3. In consequence, liquid including washing solution and blood B stored in the wide diameter portion 15b are attracted by suction pressure to flow upward and then discharged from the discharge path 17 via the narrow diameter portion 15a. Waste liquid discharged from the discharge path 17 is eventually stored in the waste liquid storage chamber 29.

Next, a method of washing the inner wall surface of the pipet 3 is described below. After completing sampling of blood 2 via the sampling valve 4, the pipet washing process is executed. More specifically, since the washing member 5 gradually descends, as shown in FIG. 3, the bottom end of the pipet 3 is eventually positioned slightly above the discharge path 17 and inside of the narrow diameter portion 15a of the through-hole 15 of the washing member 5.

While this condition remains, the first valve 23 is opened so that the washing solution storage chamber 24 can be connected to the first pump 25. When the first pump 25 is switched over to suction mode and operated, washing solution from the washing solution storage chamber 24 is sucked into the first pump 25. Next, the first valve 23 is opened so that the first pump 25 can be connected to the first tube 22. When the first pump 25 is switched over to the discharge mode and operated, washing solution in the first pump 25 is supplied to the interior of the pipet 3 via the first tube 22 and the sampling quantification unit 4. Supply of washing solution is executed for 5 seconds at 0.1 ml/sec. of flow rate. Washing solution supplied to the interior of the pipet 3 is discharged from the bottom end of the pipet 3.

Simultaneous with the process to supply washing solution into the pipet 3, washing solution is also supplied to the periphery of the pipet from the supply path 16 of the washing member 5. Since the through-hole 15 is blocked by the pipet 3, blood B and washing solution discharged from bottom end of the pipet 3 and the other washing solution fed from the supply path 16 are jointly collected in the discharge path 17 via the wide diameter portion 15b, the tapered portion 15c, and the narrow diameter portion 15a and are stored in the waste liquid storage chamber 29.

In order to more effectively execute washing, the amount of washing solution supplied to the supply path 16 of the washing member 5 may be varied according to the magnitude of the negative pressure affecting the discharge path 17.

The inner and outer wall surfaces of the pipet 3 and the inner surface of through-hole 15 of the washing member 5 are fully washed by execution of the above processes. Liquid drops are eliminated from the outer wall surface of the pipet 3 and the through-hole 15 of the washing member 5 as described previously.

Next, the drive motor 9 reverses its direction to cause the drive belt 12 to reverse direction. This in turn causes the first, second, and the third supporting members 6, 7, and 8, to gradually ascend. Thus, the washing member 5 ascends and returns to its original position. While the washing member 5 ascends, negative pressure corresponding to the above-specified magnitude is applied to the discharge path 17 of the washing member 5. Accordingly, liquid adhered to outer wall surface of the pipet 3 can more fully be removed as described previously.

When operating the pipet washing apparatus W1 according to the invention, as was described above, blood B adhered to the inner and outer wall surfaces of the pipet 3 can be fully eliminated and collected. Furthermore, due to the pipet freely entering the wide diameter portion of the through-hole even when large amounts of blood B are adhered to the outer wall of the pipet, blood B is prevented from adhering to an opening edge 15d on the bottom part of the through-hole 15 and is washed from the tapered portion 15c.

Embodiment 2

Figure 4:
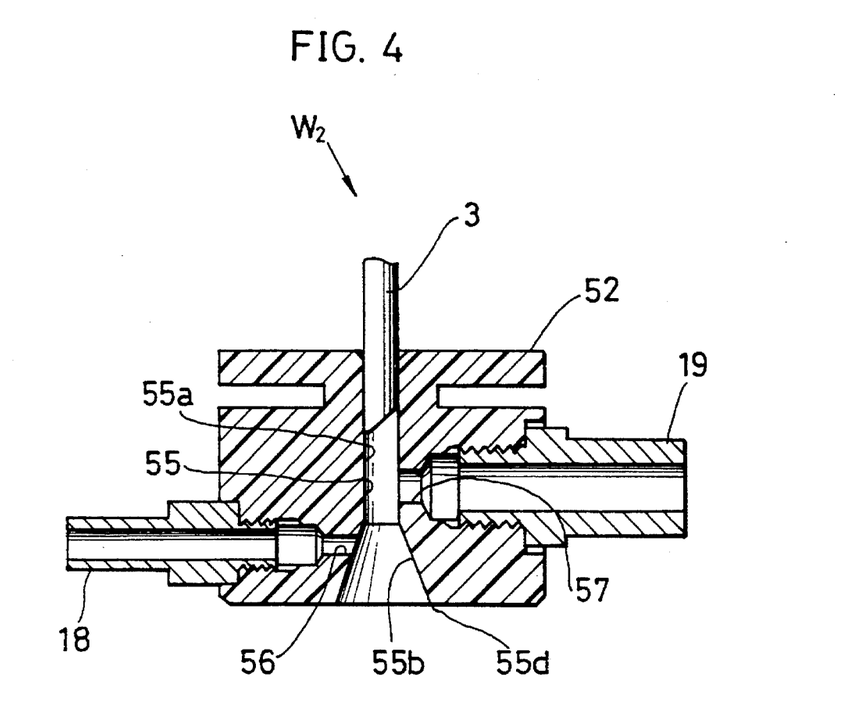
FIG. 4 is a sectional view of structural members of the pipet washing apparatus according to a second embodiment of the invention in the course of washing an inner wall surface of a pipet.

Referring now to FIG. 4, structural features of the pipet washing apparatus W2 according to a second embodiment of the invention will be described below. The washing member 52 embeds a vertically formed through-hole 55 accommodating a loosely coupled pipet 3, a horizontal supply path 56 for feeding washing solution to the through-hole 55, and a horizontal discharge path 57 for discharging washing solution and blood B from the through-hole 55. The through-hole 55, the supply path 56, and the discharge path 57 are respectively of circular sectional form.

The through-hole 55 has a narrow diameter portion 55a with a narrow clearance for the pipet 3 and a conical portion 55b extending below the narrow diameter portion 55a with increasing clearance for the pipet 3. The length (height) of the narrow diameter portion 55a corresponds to about 70% of the height of the washing member 52. The diameter of the narrow diameter portion 55a corresponds to about 115% (2.3 mm) of the outer diameter of the pipet 3. The axial length (height) of the conical portion 55b corresponds to about 30% of the height of the washing member 52. The bottom end diameter of the conical portion 55b corresponds to about 300% (6.0 mm) of the outer diameter of the pipet 3.

The diameter of the supply path 56 corresponds to about 55% of the outer diameter of the pipet 3. The inner end of the supply path 56 is open and is near the upper end of the conical portion 55b. The diameter of the discharge path 57 corresponds to about 105% of the outer diameter of the pipet 3. The inner end of the discharge path 57 is open and is near the bottom end of the narrow diameter portion 55a.

A small nipple 18 and a large nipple 19 are horizontally secured to the washing member 55 via partial embedment. The structure and function of other component members of the pipet washing apparatus W2 are identical to those of the pipet washing apparatus W1 of the first embodiment of the invention.

Like the pipet washing apparatus W1, when operating the pipet washing apparatus W2, removal and collection of blood B adhered to inner and outer wall surfaces of the pipet 3 and collection of washing solution can be fully and effectively achieved without permitting adhesion of blood B to the bottom edge 55d of the conical portion 55b.

Embodiment 3.

Figure 5:
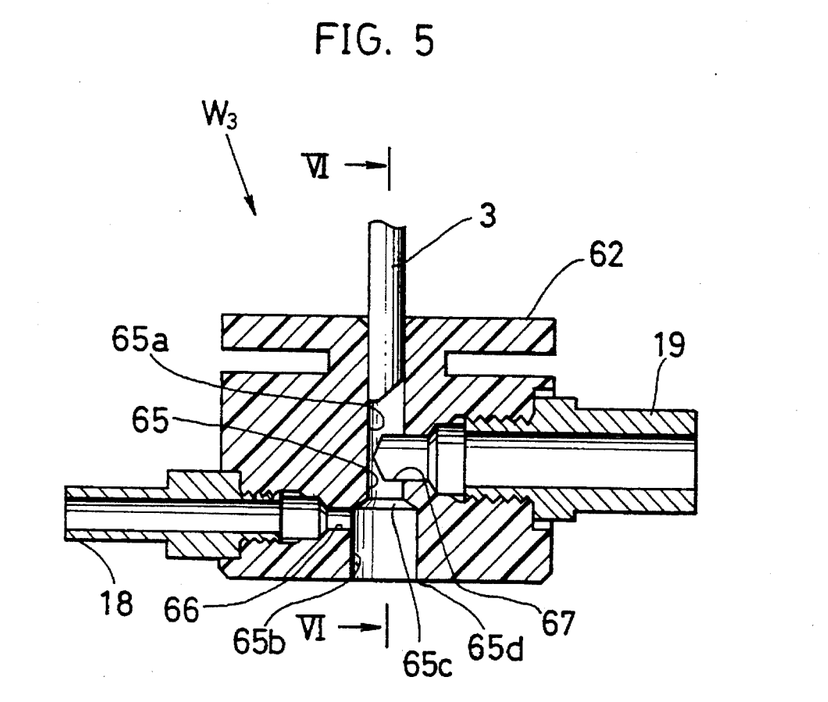
FIG. 5 is a sectional view of structural members of the pipet washing apparatus according to a third embodiment of the invention in the course of washing an inner wall surface of a pipet.
Figure 6:
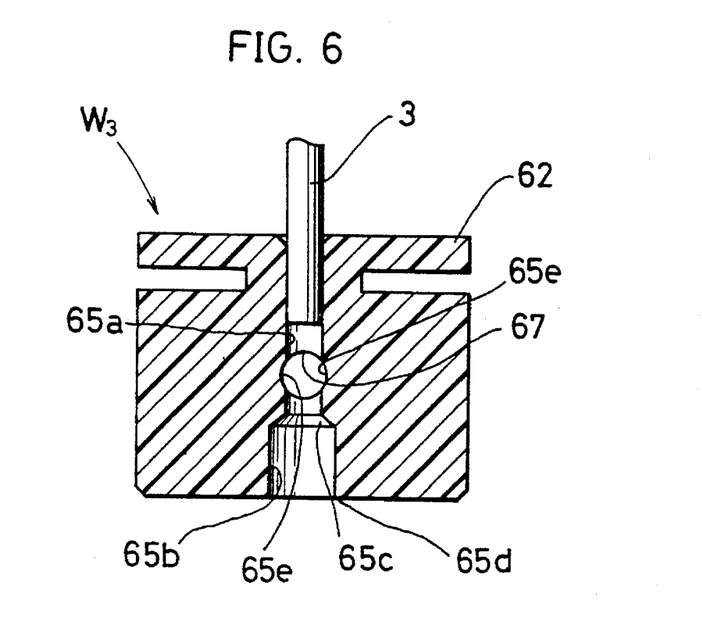
FIG. 6 is a sectional view of structural members of the pipet washing apparatus shown in FIG. 5 taken along line VI—VI.

Referring now to FIGS. 5 and 6, structural features of the pipet washing apparatus W3 according to a third embodiment of the invention will be described below. The washing member 62 embeds a vertical through-hole 65 accommodating a loosely inserted pipet 3, a horizontal supply path 66 for feeding washing solution to the through-hole 65, and a horizontal discharge path 67 for discharging washing solution and blood B from the through-hole 65. The through-hole 65, the supply path 66, and the discharge path 67 are each of circular sectional form.

The through-hole 65 has a narrow diameter portion 65a with a narrow clearance for the pipet 3 and a wide diameter portion 65b formed below the narrow diameter portion and connected 65a thereto by a tapered portion 65c. Tapered portion 65c is formed between the narrow diameter portion 65a and the wide diameter portion 65b. The length (height) of the narrow diameter portion 65a corresponds to about 70% of the height of the washing member 62, whereas the diameter of portion 65a corresponds to about 115% (2.3 mm) of the outer diameter of the pipet 3. The length (height) of the wide diameter portion 65b corresponds to about 25% of the height of the washing member 5, whereas the diameter of portion 65b corresponds to about 200% (4.0 mm) of the outer diameter of the pipet 3. The height of the tapered portion 65c corresponds to about 5% of the height of the washing member 62.

The diameter of the supply path 66 corresponds to about 55% (1.1 mm) of the outer diameter of the pipet 3. The inner end of the supply path 66 is open and is near the upper end of the wide diameter portion 65b. The diameter of the discharge path 67 corresponds to about 130% (2.6 mm) of the outer diameter of the pipet 3. The inner end of the discharge path 67 is open and is near to a bottom end of the narrow diameter portion 65a.

As was specified above, the ratio between the diameter of the inner end of the discharge path 67 and the diameter of the narrow diameter portion 65a is determined to be approximately 130:115. To implement this, as shown in FIG. 6, a pair of recessed portions 65e/65e are formed on both sides of the narrow diameter portion 65a of the through-hole 65, where the recessed portions 65e/65e make up part of the discharge path 67. Accordingly, there is no fear of the pipet 3 blocking the discharge path 67 when the pipet 3 is inserted in the through-hole 65, and thus, the efficiency in the collection of washing solution in the course of washing the outer wall surface of the pipet 3 is enhanced.

A small nipple 18 and a large nipple 19 are horizontally secured to the washing member 62 via partial embedment. The structure and function of other component members of the pipet washing apparatus W3 are identical to those of the pipet washing apparatus W1 related to the first embodiment of the invention.

Like the pipet washing apparatus W1, when operating the pipet washing apparatus W3, removal and collection of blood B adhered to the inner and outer wall surfaces of the pipet 3 and the collection of washing solution can be fully and effectively achieved without blood B adhering to the bottom edge 65d of the wide diameter portion 65b and any blood which adheres to tapered portion 65c is washed away.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A pipet washing apparatus comprising;
   a pipet-outer-wall washing member including a through-hole, in which a pipet with a bottom end serving as a sampling inlet is loosely insertable, a supply path for supplying washing solution to said through-hole, and a discharge path for discharging waste liquid from said through-hole;
   pipet-interior washing device, connectable to said pipet, for supplying washing solution to the interior of said pipet;
   a washing solution storage chamber, connected to said supply path of said pipet-outer-wall washing member and said pipet-interior washing device;
   suction device connected to said discharge path of said pipet-outer-wall washing member, for sucking up waste liquid;
   a waste liquid storage chamber, connected to said discharge path of said pipet-outer-wall washing member, for storing the waste liquid sucked-up by said suction device; and
   drive device for causing at least one of said washing member and said pipet to move, to thereby vary the relative position of said washing member and said pipet,
   said through-hole including a relatively narrow diameter portion of substantially constant diameter defining an entrance opening of relatively small clearance for insertion of said pipet, and a relatively wide diameter portion, formed below said relatively narrow diameter portion, defining an exit opening having clearance for said pipet that is relatively wider than that of said entrance opening, and wherein said supply path is directly connected to said relatively wide diameter portion and said discharge path is directly connected to said relatively narrow diameter portion such that an inner wall of the interior of the pipet is washed by supplying washing solution from the supply path, and such that waste liquid is discharged from the sampling inlet of the pipet when the sampling inlet of the pipet is positioned above the discharge path and inside the relatively narrow diameter portion of the through-hole of the washing member.

2. The pipet washing apparatus of claim 1, wherein said supply path and said discharge path of said washing member are each orthogonal to said through-hole and parallel with each other.

3. The pipet washing apparatus of claim 1, wherein said relatively wide diameter portion includes a tapered portion adjacent to said relatively narrow diameter portion of said through-hole.

4. The pipet washing apparatus of claim 1, wherein said discharge path includes a recessed portion of a wall surface of said discharge path, formed in said relatively narrow diameter portion of said through-hole.

5. The pipet washing apparatus of claim 4, wherein the ratio between an diameter of the inner end portion of the discharge path and the diameter of the relatively narrow diameter portion of the through-hole is about 130:115.

6. The pipet washing apparatus of claim 1, wherein said pipet-interior washing device includes a tube for supplying a washing solution and a pump connected to said tube via a valve.

7. The pipet washing apparatus of claim 1, wherein said suction device includes a suction pump connected to said discharge path of said pipet-outer-wall washing member via said waste liquid storage chamber.

8. The pipet washing apparatus of claim 1, wherein the diameter of the relatively narrow diameter portion of the through-hole ranges from 110% to 120% of an outer diameter of the pipet.

9. The pipet washing apparatus of claim 1, wherein said drive device includes a drive motor with a rotary shaft which is capable of rotating in either a normal or reverse direction, a first pulley linked with said rotary shaft of said drive motor, a second pulley disposed above or below said first pulley, a drive belt engaged by said first and second pulleys, and supporting members which interconnect and hold said drive belt and said washing member to move said washing member relative to the pipet.

10. The pipet washing apparatus of claim 1, wherein said supply path has a diameter of about 55% of an outer diameter of the pipet, and said discharge path has a diameter of about 105% of an outer diameter of the pipet.

11. A pipet washing apparatus comprising:
   a pipet-outer-wall washing member including a through-hole, in which a pipet with a bottom end serving as a sampling inlet is loosely insertable, a supply path for supplying washing solution to said through-hole, and a discharge path for discharging waste liquid from said through-hole;
   a pipet-interior washing device, connectable to said pipet, for supplying washing solution to the interior of said pipet;
   a washing solution storage chamber, connected to said supply path of said pipet-outer-wall washing member and said pipet-interior washing device;
   a suction device, connected to said discharge path of said pipet-outer-wall washing member, for sucking up waste liquid;

a waste liquid storage chamber connected to said discharge path of said pipet-outer-wall washing member, for storing the waste liquid sucked-up by said suction device; and a drive device for causing at least one of said washing member and said pipet to move, to thereby vary the relative position of said washing member and said pipet, said through-hole including a relatively narrow diameter portion of substantially constant diameter defining an entrance opening of relatively small clearance for insertion of said pipet, and a conical portion extending below the relatively narrow diameter portion, defining an exit opening having clearance for said pipet that is relatively wider than that of said entrance opening, the supply path being directly connected to the conical portion and the discharge path being directly connected to the relatively narrow diameter portion such that an inner wall of the interior of the pipet is washed by supplying washing solution from the supply path, and such that waste liquid is discharged from the sampling inlet of the pipet when the sampling inlet of the pipet is positioned above the discharge path and inside the relatively narrow diameter portion of the through-hole of the washing member.

12. The pipet washing apparatus of claim 11, wherein the diameter of the relatively narrow diameter portion of the through-hole ranges from 110% to 120% of an outer diameter of the pipet.

13. The pipet washing apparatus of claim 11, wherein said supply path and said discharge path of said pipet-outer-wall washing member are each orthogonal to said through-hole and parallel with each other.

14. The pipet washing apparatus of claim 11, wherein said discharge path includes a recessed portion of a wall surface of said discharge path, formed in said relatively narrow diameter portion of said through-hole.

15. The pipet washing apparatus of claim 14, wherein the ratio between the diameter of an inner end portion of the discharge path and the diameter of the relatively narrow diameter portion of the through-hole is about 130:115.

16. The pipet washing apparatus of claim 11, wherein said pipet-interior washing device includes a tube for supplying a washing solution and a pump connected to said tube via a valve.

17. The pipet washing apparatus of claim 11, wherein said suction device includes a suction pump connected to said discharge path of said pipet-outer-wall washing member via said waste liquid storage chamber.

18. The pipet washing apparatus of claim 11, wherein said drive device includes a drive motor with a rotary shaft which is capable of rotating in either a normal or reverse direction, a first pulley linked with said rotary shaft of said drive motor, a second pulley disposed above or below said first pulley, a drive belt engaged by said first and second pulleys, and supporting members which interconnect and hold said drive belt and said washing member to move said washing member relative to the pipet.

19. The pipet washing apparatus of claim 11, wherein said supply path has a diameter of about 55% of an outer diameter of the pipet, and said discharge path has a diameter of about 105% of an outer diameter of the pipet.

* * * * *